United States Patent [19]
Heaven et al.

[11] Patent Number: 5,439,469
[45] Date of Patent: Aug. 8, 1995

[54] WOUND CLOSURE DEVICE

[75] Inventors: Malcolm D. Heaven, Hopewell; Howard Schrayer, Princeton, both of N.J.

[73] Assignee: Advanced Surgical, Inc., Princeton, N.J.

[21] Appl. No.: 145,855

[22] Filed: Nov. 5, 1993

[51] Int. Cl.⁶ ............................................. A61B 17/00
[52] U.S. Cl. .................................. 606/144; 606/139; 606/223; 112/169; 112/222; 289/16; 223/102
[58] Field of Search ............... 606/139, 144, 145, 147, 606/148, 222, 223; 112/80.03, 169; 289/16; 223/102, 104

[56] References Cited

U.S. PATENT DOCUMENTS

| 385,586 | 7/1888 | Woods | 112/169 |
|---|---|---|---|
| 2,738,790 | 3/1956 | Todt, Sr. et al. | 606/144 |
| 4,890,614 | 1/1990 | Kawada et al. | 606/226 |
| 5,192,287 | 3/1993 | Fournier et al. | |
| 5,217,470 | 6/1993 | Weston | |
| 5,217,471 | 6/1993 | Burkhart | |
| 5,222,508 | 6/1993 | Contarini | |
| 5,234,443 | 8/1993 | Phan et al. | |
| 5,236,443 | 8/1993 | Sontag | |
| 5,254,105 | 10/1993 | Haaga | |
| 5,258,000 | 11/1993 | Gianturco | |
| 5,281,237 | 1/1994 | Gimpelson | 606/148 |
| 5,308,353 | 5/1994 | Beurrier | 606/144 |
| 5,318,577 | 6/1994 | Li | 606/147 |
| 5,320,632 | 6/1994 | Heidmuller | 112/169 |
| 5,336,239 | 8/1994 | Gimpelson | 606/223 |
| 5,350,385 | 9/1994 | Christy | |

FOREIGN PATENT DOCUMENTS

| 0529675A2 | 3/1993 | European Pat. Off. | |
|---|---|---|---|
| 1093329 | 5/1984 | U.S.S.R. | 606/145 |
| 1115736 | 9/1984 | U.S.S.R. | 606/222 |
| WO92/12674 | 8/1992 | WIPO | 606/139 |
| WO92/19313 | 11/1992 | WIPO | |
| WO93/13714 | 7/1993 | WIPO | |
| WO93/21831 | 11/1993 | WIPO | |

Primary Examiner—Stephen C. Pellegrino
Assistant Examiner—Jeffrey A. Schmidt
Attorney, Agent, or Firm—Burns, Doane, Swecker & Mathis

[57] ABSTRACT

A suture device including a hook needle, a body portion which fits within a wound site and a handle portion pivotally attached to the body portion. The needle is J-shaped with a long straight part and short curved part terminating in a pointed end. The long part of the needle slides in a channel in the handle portion and the pointed end moves axially toward and away from the handle with the curved part of the needle facing internal organs during closure of a wound site in an abdominal cavity.

20 Claims, 6 Drawing Sheets

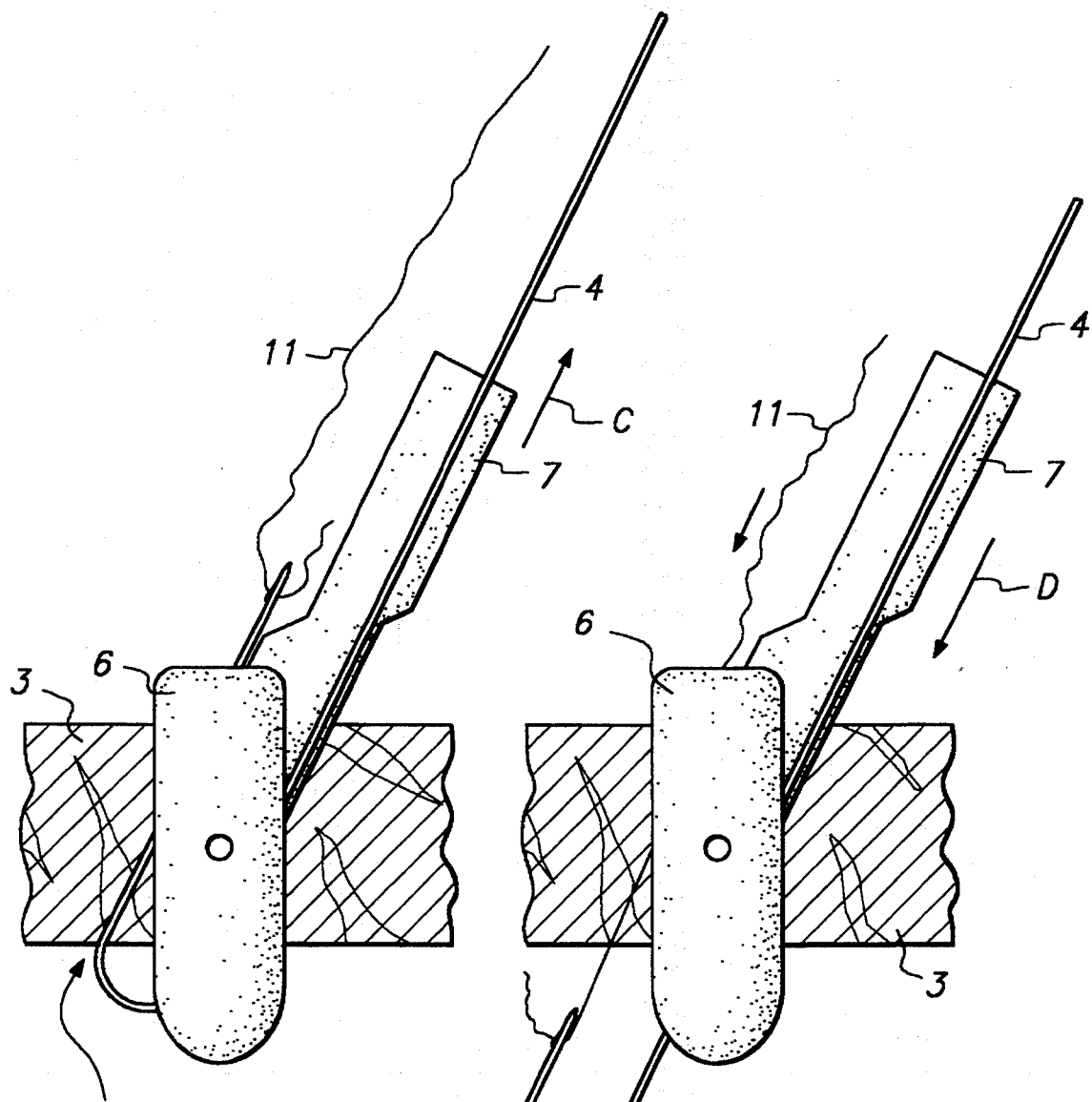

WOUND CLOSURE DEVICE

FIELD OF THE INVENTION

This invention relates to a device to enable the closure of the puncture wounds made by trocars used in laparoendoscopic procedures. Specifically, the device allows the proximating of the peritoneal membrane and the posterior wall of the fascia (the inner layers of the abdominal wall) by passing a suture through these structures thus permitting placement of a subcutaneous surgical suture knot.

BACKGROUND OF THE INVENTION

Current laparoendoscopic practices require that the abdomen be filled with an inert gas such as carbon dioxide (insuffiated). This expands the abdominal cavity and allows the surgeon a working space between the patient's internal organs and the peritoneal wall. Once the cavity is expanded, surgical access is gained by puncturing the abdominal wall with a trocar and inserting a cannula. At the completion of the surgical procedure, it is considered desirable to close the puncture sites and thereby minimize the risk of wound infection, dehiscence and incisional hernia. This closure would classically be accomplished with a needle and suture.

In order to minimize the risk of injury to internal organs when a suture needle is inserted into the abdominal wall, the maintenance of abdominal expansion (pneumoperitoneum) is essential. Additionally, to ensure proper wound closure, the suture needle must be inserted at an angle which allows approximation of the innermost structures (i.e peritoneal wall and posterior fascia).

Several methods have been proposed for performing wound closure in laparoendoscopic procedures, among which there may be mentioned a device attributed to Grice. However, the prior art wound closure devices provide inadequate means of closing the trocar wound. In particular, the prior art devices have several problems. First, some devices do not provide a method to maintain insufflation of the abdominal cavity (pneumoperitoneum), as they require the removal of the cannula prior to the introduction of the suture instrument into the wound. This allows the insufflating gas to escape from the abdomen, thus partially or fully deflating the abdomen and further increasing the risk of perforating an internal organ.

Additionally, other devices do not provide any method for gauging the proper angle to capture the tissue to be proximated. The surgeon inserts the needle "free-hand" into the abdominal wall and must only assume that when the needle emerges through the fascia, it is in the correct angle.

Many of the prior art devices also require the use of additional instruments to complete the procedure. In other designs, once the needle is initially inserted through the abdominal wall, the control of the suture is transferred from the needle to a grasper. The grasper retains the suture until the needle can be removed and reinserted on the opposite side of the puncture wound. Using the grasper, the surgeon must then rethread the suture into the needle before the needle can be withdrawn, thus completing the suture loop. The entirety of this procedure must be done under direct vision. This requires that the surgeon devote both hands to the procedure, in addition to requiring an assistant to position the laparoscope and assist in attaching the suture to the needle on its second insertion.

Finally, some instruments require that the suture be threaded through the entire length of a hollow insertion needle, which makes use of such devices time consuming and difficult.

The present invention provides solutions to the various problems noted above with respect to the prior art wound closure devices, and methods of manufacturing such devices.

SUMMARY OF THE INVENTION

The invention provides a suture device comprising a hook needle and a guide member. The needle has a distal portion extending between a longitudinally extending manipulating portion and a longitudinally extending pointed end of the needle, the pointed end of the needle including a suture holding member. The guide member has a guide channel receiving the manipulating portion of the needle and the manipulating portion of the needle is movable in the guide channel so as to advance and retract the pointed end of the needle toward and away from the guide member.

According to one embodiment of the invention, the guide member comprises a body portion pivotally connected to a handle portion. The body portion extends in a longitudinal direction and the handle portion is pivotally connected to the body portion so as to pivot about a pivot axis extending perpendicular to the longitudinal directions. The body portion includes a fiat surface in sliding contact with a flat surface of the handle portion. A pivot pin pivotally connects the handle portion to the body portion such that a distal end of the handle portion is located between the pivot pin and a distal end of the body portion. The handle portion includes a proximal end and the body portion includes a proximal end located between the pivot pin and the proximal end of the handle portion.

The suture holding member can comprise an eye opening in the pointed end of the needle for attaching a suture to the needle. The suture holding member can also comprise a spring loaded entrapment mechanism or any other suitable means. The needle is preferably a non-tubular piece of metal such as wire. The device can further comprise a tubular member of a trocar surrounding the guide member such that the guide member is slidably received in the tubular member and provides a fluid-tight seal therebetween. The guide member can be of a polymer or metal material and the handle portion and body portion can each be of a polymer or metal material.

According to another embodiment, the body portion includes a longitudinally extending slot which opens along one side of the body portion. The needle is movable in the slot such that the needle is completely within the slot when the manipulating portion is pulled away from the guide member and the pointed end of the needle is moved out of the slot when the manipulating portion is pushed toward the guide member. The slot can include seal means such as one or more rubber gaskets which maintains a fluid tight seal with the needle when the needle moves in the slot and the pointed end of the needle passes through the seal means.

The invention also provides a method of forming a subcutaneous tissue closure with a suture device including a hook needle and a guide member, the needle being movable toward and away from the guide member and being pivotal with respect to the guide member. The method includes steps of:
(a) inserting the suture device in a wound site extending through tissue of a living body,
(b) pivoting the needle from a first orientation to a second orientation,
(c) moving the needle in a first direction until a pointed end of the needle pierces the tissue and the pointed end of the needle is located on an outer side of the tissue,
(d) attaching a suture to the pointed end of the needle,
(e) moving the needle in a second direction until the pointed end of the needle is located on an inner side of the tissue,
(f) orienting the needle from the second orientation to a third orientation,
(g) moving the needle in a third direction until the pointed end of the needle pierces the tissue and the pointed end is on the outer side of the tissue,
(h) removing the suture from the needle,
(i) moving the needle in a fourth direction until the pointed end of the needle is located on the inner side of the tissue,
(j) pivoting the needle from the third orientation to the first orientation,
(k) removing the suture device from the wound site and
(l) tying a knot in the suture.

The suture device can be rotated about an axis passing through the wound site during the orienting step (f). The needle can slide through a guide channel in the guide member when the needle is moved during the needle moving steps (c, e, g and i). The pointed end of the needle can be angled so as to pass only through the inner side of the tissue and into the wound side in the tissue without piercing the outer side of the tissue during the steps (c and g) of moving the needle in the first and third directions.

BRIEF DESCRIPTION OF THE DRAWINGS

FIG. 5 shows the hook needle being advanced outwardly through the abdominal wall for attachment of a suture to a hook end of the needle at a location outside the abdominal cavity;

FIG. 6 shows the needle after it is retracted into the abdominal cavity with the suture attached;

DETAILED DESCRIPTION OF THE INVENTION

Figure 1:
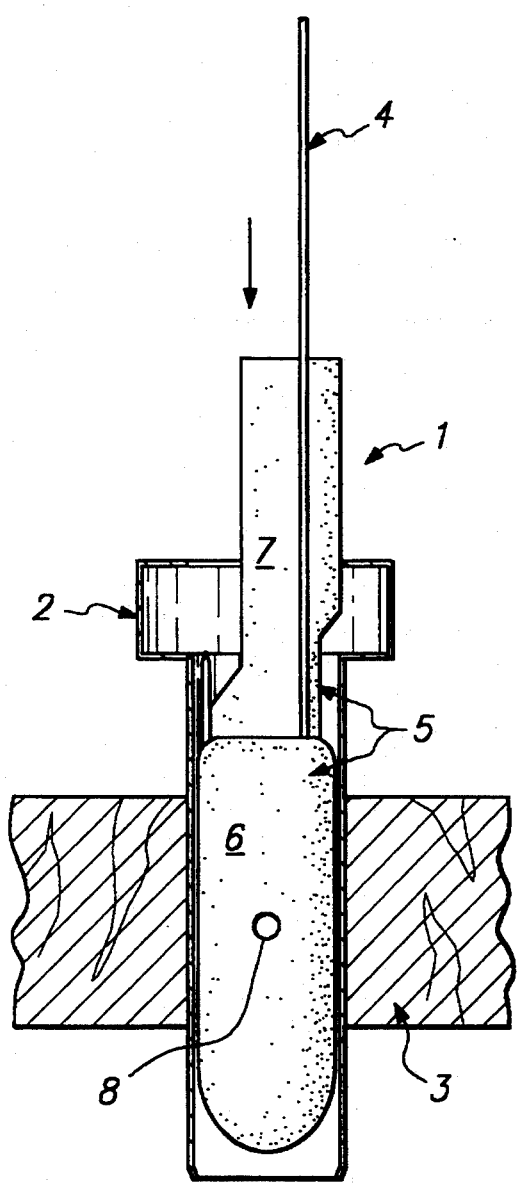
FIG. 1 is a side view of a suture device for closing a wound site in accordance with the invention (obturator, movable handle and needle), showing the device placed into a trocar located in an abdominal wall of a living body.

The invention provides a medical device usable within a body cavity. The device includes a hooked needle and an obturator (guide member), which is sized to fit intimately within a cannula. The guide member serves to maintain the pneumoperitoneum following exchange with the cannula. The guide member can be of single piece or multipiece construction. In the multipiece construction, a pivoting handle is attached to a body portion of the guide member by means of a rivet or rod which allows the handle to swivel to adjust the angle for insertion of the hooked needle. The swivel movement of the handle will correspond to the angle of the needle inside the body providing the surgeon with a method to easily judge the angle of needle insertion into the peritoneal wall. The same effect can also be achieved using a single piece guide member by simply tilting the guide member back and forth to the desired angle. The curved portion of the needle is housed at the proximal end of the body portion and can be withdrawn or advanced by manipulating the needle shaft which extends through the body portion and beyond a proximal end of the handle of the device. The hooked needle is pulled outward to pass the suture through the tissue layers, thus eliminating the risk of passing a sharp needle from outside the body toward the internal organs.

The body member is designed to fit snugly inside the cannula and allows the cannula to be removed over it, leaving the device body to fill the puncture wound. For instance, the body member is preferably round in shape to allow maintenance of the pneumoperitoneum. Once the cannula is removed, the hooked needle shaft can be advanced into the abdominal cavity. The shape of the hooked needle reduces the risk of internal injury as the part of the needle which advances toward internal organs is rounded rather than sharply pointed. The surgeon then can manipulate the device handle to the correct angle. Upon reaching the correct angle, the needle is withdrawn toward the operator through the peritoneal wall and fascia. When the needle emerges from the subcutaneous tissue, a suture is threaded into the needle or captured by a spring-loaded trap mechanism just behind the needle tip. This is done outside the body. The suture needle is then pushed back through the abdominal wall with the suture attached. Once the needle is completely within the abdominal cavity, the device body is rotated 180 degrees and the needle is again pulled through the abdominal wall towards the operator. The suture is removed from the needle or capture mechanism. At this point, the two free ends of the suture remain outside the body. The needle is then pushed back through the abdominal wall. Once the needle is completely inside the abdominal cavity, the device handle is returned to its vertical position, the needle is withdrawn into the device body and the device is withdrawn from the wound. The suture knot can then be tied, leaving a suture knot in the subcutaneous tissue.

According to various aspects of the invention, the obturator can comprise a polymeric material selected from the group consisting of ABS, polycarbonate, nylons, blends or other suitable polymers and mixtures thereof. The obturator could also be stainless steel or some other suitable material should a reusable, rather than a disposable device be required.

The invention is now described with reference to FIGS. 1-10 which show one embodiment of a suture device in accordance with the invention. In particular, FIG. 1 is a side view showing the suture device 1 placed into a trocar 2 located in an abdominal wall 3 of a living body. The device 1 includes a needle 4 and a guide member 5. The guide member 5 includes a body portion 6 and a handle portion 7 pivoted to the body portion 6 by means of a pivot pin 8.

Figure 2:
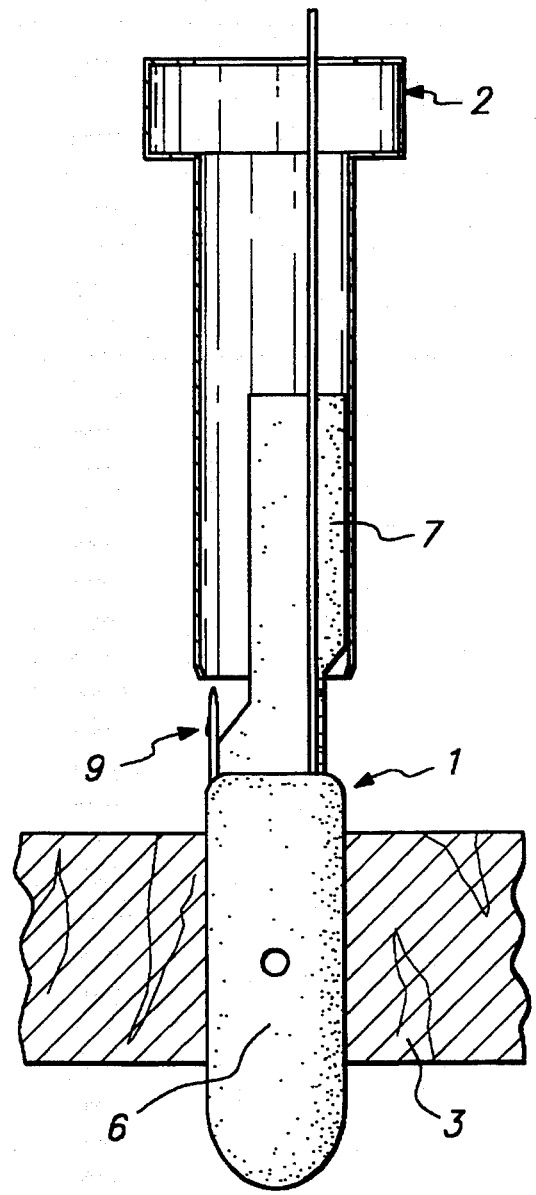
FIG. 2 is a side view showing the device remaining in place as the trocar/cannula is removed, with the central body section maintaining pneumoperitoneum.

FIG. 2 is a side view showing the device 1 remaining in place as the trocar/cannula 2 is removed, with the central body portion 6 maintaining pneumoperitoneum. The needle 4 includes a suture attaching mechanism for attaching a suture to the pointed end of the needle 4.

Figure 3:
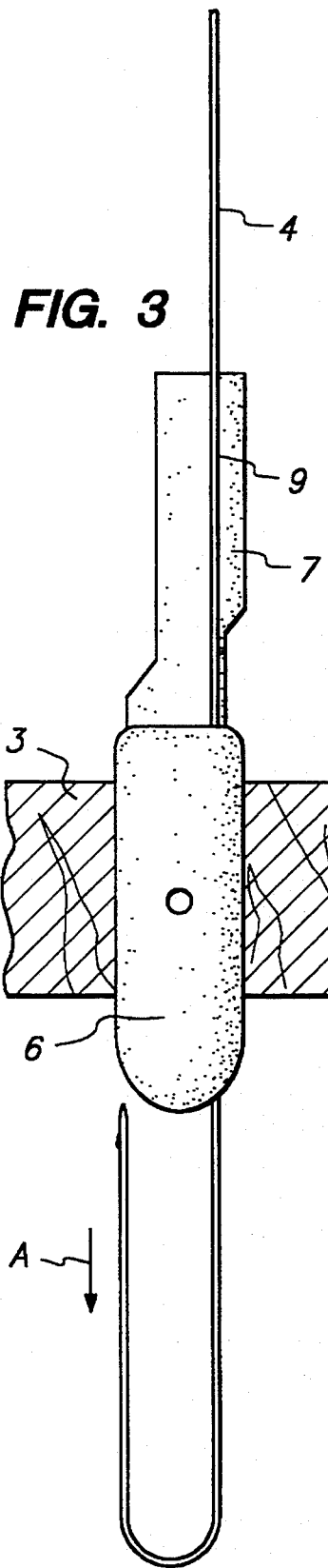
FIG. 3 shows a side view as the hook needle is advanced inwardly into the abdominal cavity.

FIG. 3 shows a side view as the needle 4 is advanced inwardly into the abdominal cavity. In particular, the needle 4 is slid in the direction indicated by arrow A in channel 9 until the pointed end of the needle is below the abdominal wall 3.

Figure 4:
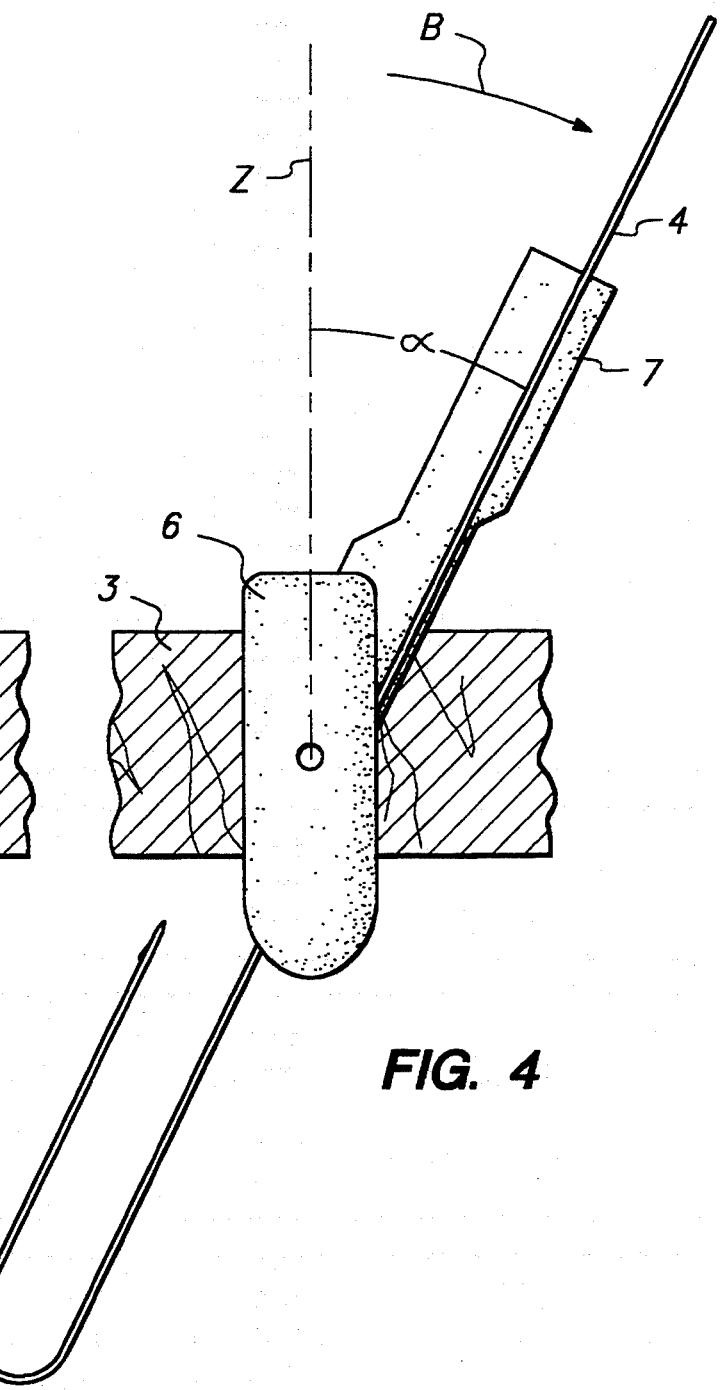
FIG. 4 shows the handle pivoted to a desired angle to allow the hook needle to appropriately capture sufficient tissue to secure a suture.

FIG. 4 shows the handle 7 pivoted in the direction indicated by arrow B to a desired angle α with respect to body axis to allow the needle 4 to appropriately capture sufficient tissue to secure a suture. Thus, the pointed end of the needle 4 is below the abdominal wall 3 and positioned for passing through the wall in a direction away from internal organs.

FIG. 5 shows the needle 4 being advanced outwardly in the direction indicated by arrow C through the abdominal wall 3 for attachment of a suture 11 to mechanism 9 at a location outside the abdominal cavity.

FIG. 6 shows the needle 4 after it is retracted in the direction indicated by arrow D into the abdominal cavity with the suture 11 attached to the end of the needle.

Figures 7, 8:
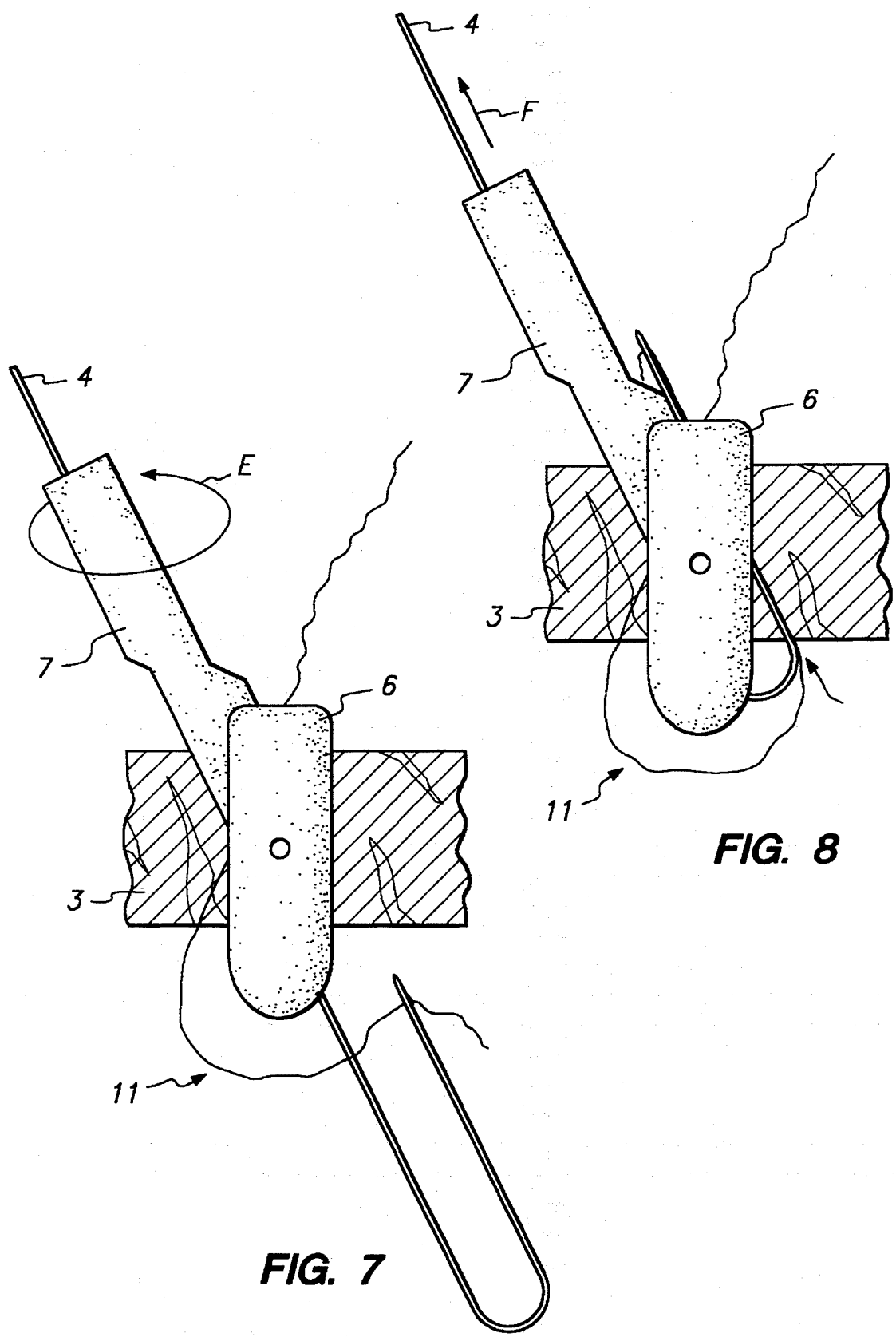
FIG. 7 shows the device after being rotated 180 degrees about the device axis.
FIG. 8 shows the hook needle advanced outwardly for detachment of the suture from the needle through the abdominal wall and into the subcutaneous space for detachment of the suture from the needle.

FIG. 7 shows the device after being rotated 180 degrees in the direction indicated by arrow E about the body axis Z.

FIG. 8 shows the needle 4 advanced outwardly in the direction indicated by arrow F for detachment of the suture 11 from the needle 4. That is, the suture 11 can be removed from the attachment mechanism 9 after the needle passes outwardly through the abdominal wall 3 and into the subcutaneous space.

Figures 9, 10:
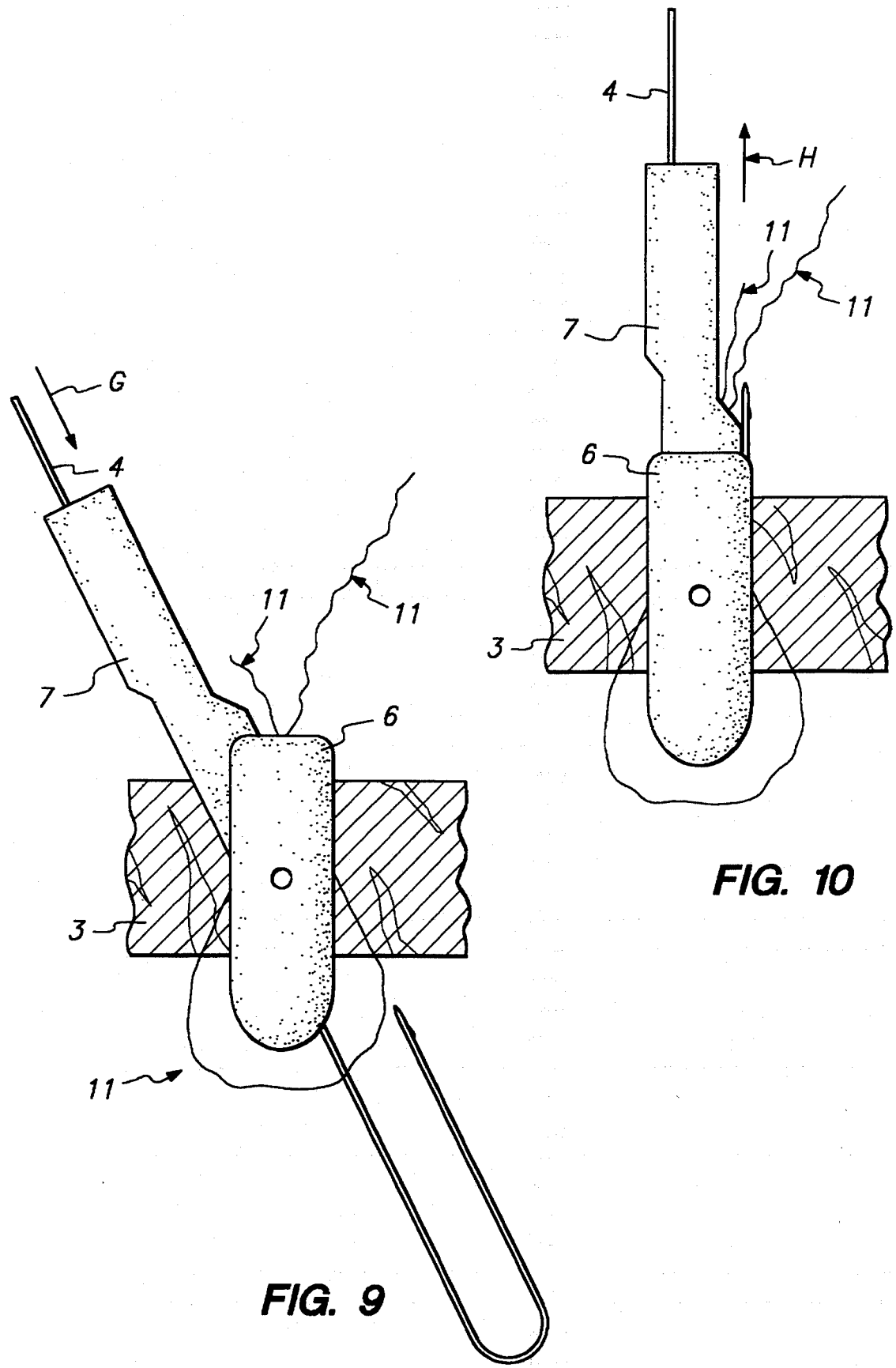
FIG. 9 shows the needle after detachment of the suture from the needle and after being retracted into the abdominal cavity.
FIG. 10 shows the handle pivoted into alignment with the central body, the needle withdrawn into the obturator and the device being withdrawn from the wound site. The two ends of the suture remain outside the body in the subcutaneous space.

FIG. 9 shows the needle 4 after the suture 11 is removed and the needle has been retracted in the direction indicated by arrow G through the abdominal wall 3. At this point, the suture 11 now encircles the puncture wound. FIG. 10 shows the handle 7 pivoted into alignment with the central body 6. Once the needle 4 is withdrawn in the direction indicated by arrow H into the guide member 5, the device 1 can be withdrawn in direction H from the wound site leaving behind the suture 11 with its two ends outside the body in the subcutaneous space.

Figure 11:
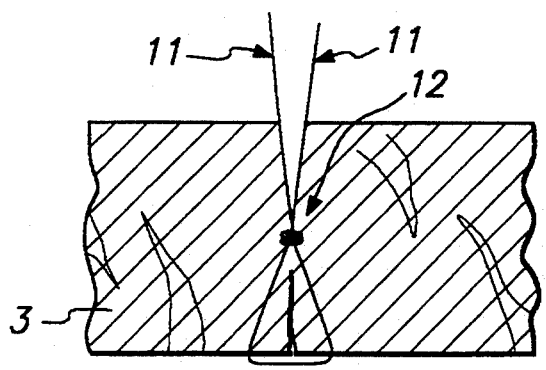
FIG. 11 shows the tying of a subcutaneous knot.

FIG. 11 shows the tying of a subcutaneous knot 12 after the device 1 has been withdrawn from the wound site. As can be seen from FIG. 11, because the needle 4 previously passed through the inner surface of the abdominal wall 3 and into the opposed surfaces of the wound site rather than through the outer surface of the abdominal wall 3, the knot 12 can be located approximately half-way below the outer surface of the abdominal wall. Thus, the knot 12 can be buried in the wound site and promote faster healing of the wound site.

Figure 12:
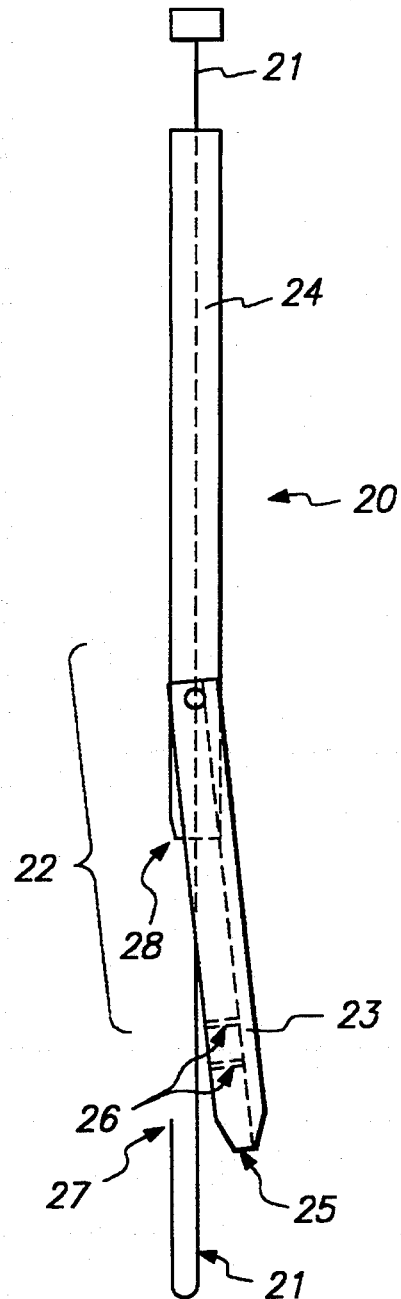
FIG. 12 shows another embodiment of the suture device according to the invention.

FIG. 12 shows another embodiment of a suture device 20 in accordance with the invention. The device 20 includes a hook needle 21, a guide member 22 including a body portion 23 and a handle portion 24. The handle portion 24 includes an axially extending hole which slidably receives the manipulating portion of the needle and the body portion 23 includes a slot 25 which slidably receives the pointed end of the needle. The slot 25 extends through the distal end of the body portion 23 and seal means 26 is provided in the slot 25 for providing a fluid tight seal with the needle when the pointed end 27 of the needle passes through or out of the seal means 26. FIG. 12 shows the handle portion 24 pivoted with respect to the body portion 24 and the needle 21 in a nearly fully extended position with the pointed end 27 outside the slot 25 and ready to pierce through the inner side of tissue surrounding a wound site. Further, the handle portion 24 includes a tapered groove 28 at a distal end thereof. The groove 28 bends the pointed end 27 of the needle outwardly when the pointed end of the needle is advanced toward and slides along the groove 28 whereby the sharp tip of the needle is held against the handle portion and the suture attaching eyelet in the pointed end of the needle is easier to thread with a suture.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. A suture device comprising:
   a hook needle having a distal portion extending between a longitudinally extending manipulating portion and a longitudinally extending pointed end of the needle, the pointed end of the needle including means for attaching a suture to the needle; and
   a guide member having a guide groove receiving the manipulating portion of the needle, the manipulating portion of the needle being slidable in the guide groove so as to advance and retract the pointed end of the needle toward and away from the guide member, the guide member being sized to fit intimately within a cannula used to introduce the guide member within a body cavity and the guide member maintaining pneumoperitoneum following exchange with the cannula.

2. The suture device of claim 1, wherein the guide member comprises a body portion pivotally connected to a handle portion.

3. The suture device of claim 2, wherein the body portion extends in a longitudinal direction and the handle portion is pivotally connected to the body portion so as to pivot about a pivot axis extending perpendicular to the longitudinal direction.

4. The suture device of claim 2, wherein the body portion includes a flat surface in sliding contact with a flat surface of the handle portion.

5. The suture device of claim 2, wherein the body portion includes a slot therein, the slot forming the guide groove which slidably supports the manipulating portion of the needle.

6. The suture device of claim 1, wherein the guide member is round in shape and the needle is J-shaped.

7. The suture device of claim 2, wherein a pivot pin pivotally connects the handle portion to the body portion.

8. The suture device of claim 7, wherein the handle portion includes a distal end located between the pivot pin and a distal end of the body portion.

9. The suture device of claim 7, wherein the handle portion includes a proximal end, the body portion including a proximal end located between the pivot pin and the proximal end of the handle portion.

10. The suture device of claim 1, wherein the suture attaching means comprises an opening in the pointed end of the needle.

11. The suture device of claim 2, wherein the handle portion includes a longitudinally extending tapered groove which slidably engages and bends the pointed end of the needle outwardly away from the handle portion when the pointed end of the needle is advanced toward and slides along the tapered groove.

12. The suture device of claim 1, wherein the needle comprises a metal wire.

13. The suture device of claim 1, further comprising a tubular member of a trocar surrounding the guide member such that the guide member is slidably received in the tubular member and provides a fluid-fight seal therebetween.

14. A suture device comprising:
a hook needle having a distal portion extending between a longitudinally extending manipulating portion and a longitudinally extending pointed end of the needle, the pointed end of the needle including means for attaching a suture to the needle: and
a guide member having a guide channel receiving the manipulating portion of the needle, the manipulating portion of the needle being slidable in the guide channel so as to advance and retract the pointed end of the needle toward and away from the guide member, the guide member including a slot and seal means in the slot for maintaining a fluid tight seal with the needle, the needle being movable in the slot such that the pointed end of the needle passes through the seal means when the needle is advanced and retracted.

15. The suture device of claim 1, wherein the guide member is of a polymer or metal material.

16. The suture device of claim 2, wherein the handle portion and body portion are each of a polymer or metal material.

17. A method of forming a subcutaneous tissue suture with a suture device including a needle and a guide member, the needle being movable toward and away from the guide member and being pivotal with respect to the guide member, comprising steps of:
inserting the suture device in a wound site extending through tissue of a living body;
pivoting the needle from a first orientation to a second orientation;
moving the needle in a first direction until a pointed end of the needle pierces the tissue and the pointed end of the needle is located on an outer side of the tissue;
attaching a suture to the pointed end of the needle;
moving the needle in a second direction until the pointed end of the needle is located on an inner side of the tissue;
orienting the needle from the second orientation to a third orientation;
moving the needle in a third direction until the pointed end of the needle pierces the tissue and the pointed end is on the outer side of the tissue;
removing the suture from the needle;
moving the needle in a fourth direction until the pointed end of the needle is located on the inner side of the tissue;
pivoting the needle from the third orientation to the first orientation;
removing the suture device from the wound site; and
tying a knot in the suture.

18. The method of claim 17, wherein the suture device is rotated about a longitudinal axis passing through the wound site during the orienting step.

19. The method of claim 17, wherein the needle slides through a guide channel in the guide member when the needle is moved during the needle moving steps.

20. The method of claim 17, wherein the pointed end of the needle can be angled to pass only through the inner side of the tissue and into the wound site in the tissue without piercing the outer side of the tissue during the steps of moving the needle in the first and third directions.

* * * * *